United States Patent [19]

Gatto

[11] Patent Number: 5,424,349

[45] Date of Patent: *Jun. 13, 1995

[54] AMIDE ANTIOXIDANTS

[75] Inventor: Vincent J. Gatto, Baton Rouge, La.

[73] Assignee: Albemarle Corporation, Richmond, Va.

[*] Notice: The portion of the term of this patent subsequent to Apr. 7, 2009 has been disclaimed.

[21] Appl. No.: 98,354

[22] PCT Filed: Feb. 26, 1992

[86] PCT No.: PCT/US92/01559

§ 371 Date: Aug. 9, 1993

§ 102(e) Date: Aug. 9, 1993

[87] PCT Pub. No.: WO92/16495

PCT Pub. Date: Oct. 1, 1992

[51] Int. Cl.⁶ .............. C08K 5/20; C07C 233/65
[52] U.S. Cl. .............. 524/222; 252/475; 252/5.15 A; 252/402; 252/403; 106/186; 524/169; 524/219; 530/427; 564/92; 564/99; 564/182; 564/219; 564/153; 564/156
[58] Field of Search .............. 564/156, 182, 279; 524/222, 217; 252/403, 51.5 A

[56] References Cited

U.S. PATENT DOCUMENTS

| | | | |
|---|---|---|---|
| 4,098,760 | 7/1978 | Cornell | 524/217 |
| 4,100,191 | 7/1978 | Fischer et al. | 564/156 |
| 5,103,054 | 4/1992 | Gatto | 564/99 |
| 5,130,484 | 7/1992 | Gatto | 564/129 |

FOREIGN PATENT DOCUMENTS 0029090 5/1981 European Pat. Off.
7905000 3/1980 Netherlands.

*Primary Examiner*—Shailendra Kumar
*Attorney, Agent, or Firm*—Richard J. Hammond; Patricia J. Hogan

[57] ABSTRACT

Tertiary amides have been developed which have low volatility and good thermal stability and which are effective in stabilizing organic materials that are normally susceptible to oxidative deterioration. The novel antioxidants are tertiary amides corresponding to the formula:

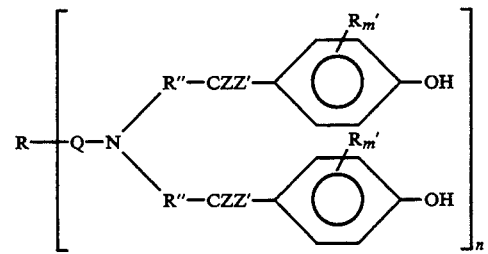

wherein R is a mono-, di-, or trivalent aromatic or saturated aliphatic hydrocarbon group containing 1–20 carbons; n is an integer of 1–3 which is equal to the valence of R; R' is phenyl, benzyl, or $C_1$–$C_6$ alkyl; m is an integer of 1–3; R'' is a $C_1$–$C_4$ alkylene group; Z and Z' are independently selected from hydrogen and alkyl; and Q is carbonyl or sulfonyl.

13 Claims, No Drawings

AMIDE ANTIOXIDANTS

This application is a 371 of PCT/U.S. Ser. No. 92/01559 filed Feb. 26, 1992.

FIELD OF INVENTION

This invention relates to novel amides having utility as antioxidants.

BACKGROUND

Many organic materials, such as polymers, fuels, and lubricants, are normally susceptible to oxidative deterioration and tend to suffer severe degradation and/or discoloration during processing and/or later use unless they are stabilized.

The compounds which have previously been proposed for use in stabilizing these materials have frequently been phenolic compounds, and some such compounds have been very successfully employed as antioxidants for some of the normally oxidizable materials. However, no single compound could be the best possible antioxidant for each of the variety of organic materials which are normally susceptible to oxidative deterioration, since:

(1) the compounds which have the lowest volatility and highest thermal stability are not necessarily those which have the most suitable melting points, the least tendency to degrade to highly-colored compounds, and the greatest ability to stabilize organic materials during processing, (2) some of the organic materials (e.g., the polymers) are less capable than others (e.g., fuels and lubricants) of tolerating the substantial discoloration that occurs when many phenolic compounds are subjected to processing conditions, (3) some antioxidant compounds are so volatile and have such poor thermal stability that they are unsuitable for use in organic materials for which high processing temperatures and/or long-term stabilization are required, and (4) some antioxidant compounds have melting points so high as to present a drawback to their use in materials which must be processed at low or moderate temperatures.

Thus, it is necessary to have different antioxidants to serve the different needs of the various organic materials which require stabilization.

Because of the need for these different antioxidants for different organic materials, it would be desirable to be able to find a class of antioxidants which could be derived from a common intermediate or a common genus of intermediates that could be easily modified so as to provide the different antioxidant properties required in the variety of specific market needs.

As disclosed in U.S. Pat. Nos. 3,780,103 (Knell), 3,808,273 (Burdet et al.), 3,927,091 (Huber-Emden et al.), 3,996,194 (Gencarelli et al.), 4,098,760 (Cornell), 4,100,191 (Fischer et al.), and 4,132,702 (Schmidt et al.) and Netherlands Patent Application 7905000 (Cincinnati Milacron Chemicals), it is known that some amides containing substituted hydroxyphenyl groups have been found to be useful as stabilizers for some organic materials which are normally susceptible to oxidative deterioration.

N,N-bis(3,5-di-t-butyl-4-hydroxybenzyl)acetamide is disclosed by G. A. Nikiforov et al. in *Izvestiya Akademii Nauk SSSR, Seriya Khimicheskaya*, No. 12, pp. 2765-2770, 1989.

SUMMARY OF INVENTION

The invention resides in (1) tertiary amides corresponding to the formula:

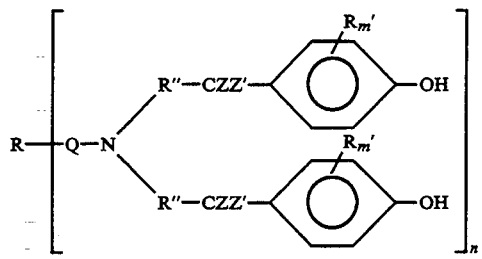

wherein R is a mono-, di-, or trivalent aromatic or saturated aliphatic hydrocarbon group containing 1-20 carbons; n is an integer of 1-3 which is equal to the valence of R; R' is phenyl, benzyl, or $C_1$-$C_6$ alkyl; m is an integer of 1-3; R'' is a $C_1$-$C_4$ alkylene group; Z and Z' are independently selected from hydrogen and alkyl; and Q is carbonyl or sulfonyl and (2) the use of the tertiary amides as antioxidants for organic materials which are normally susceptible to oxidative deterioration.

DETAILED DESCRIPTION

The novel tertiary amides of the invention are amides containing alkyl-substituted hydroxyphenyl groups which are separated from the amido nitrogens by a linking chain of at least two carbons. This type of linkage is an important feature of the compounds, since it provides lower volatility and higher thermal stability than a linkage constituted by a single carbon and thus makes the compounds superior to the corresponding compounds containing the shorter linkage, e.g., the compounds of Nikiforov et al.

As indicated by the formula, the p-alkyl substitutent represented by CZZ'R'' may have a branched chain when R'' is a branched alkylene group and/or at least one of Z and Z' is alkyl (usually an alkyl of only 1-4 carbons). However, it is generally preferred for that substituent to be unbranched except for the branching provided with Z is methyl; and it is apt to be most preferred for the R'' alkylene group to be unbranched and for Z and Z' to be hydrogen so that the CZZ'R'' of the formula is a —$(CH_2)_p$ group in which p is an integer of 2-5.

As also indicated by the formula, (1) the novel tertiary amides may be derivatives of aliphatic or aromatic carboxamides, diamides, triamides, or the corresponding sulfonamides which provide an R hydrocarbon group of up to 20 carbons, and (2) the R' substituents on the p-hydroxyphenylalkyl groups may be 1-3 in number; may be phenyl, benzyl, or $C_1$-$C_6$ alkyl; and, when there is more than one, may be the same or different. However, it is usually preferred that there be two such substituents, which are most commonly alkyl groups containing 1-4 carbons, in the positions ortho to the hydroxy group.

Exemplary of the novel tertiary amides of the invention are the (1) acetamides, propionamides, isopropionamides, butyramides, palmitamides, stearamides, and benzamides, (2) diamides of malonic, succinic, glutaric, adipic, dodecanoic, tetradecandioic, hexadecandioic, dicarboxycyclohexane, phthalic, isophthalic, and terephthalic acids, (3) triamides of 1,2,3-propanetricarboxylic, 2,3-dimethyl-1,2,3-butanetricarboxylic, and 1,2,4- and 1,3,5-benzenetricarboxylic acids, and (4) corresponding sulfonamides, such as the methanesulfonamides, propanesulfonamides, and benzenesulfonamides in which the N-substituents are β-(3,5-di-t-butyl-4-hydroxyphenyl)ethyl, β-(3-methyl-5-t-butyl-4-hydroxyphenyl)ethyl, β-(3,5-diphenyl-4-hydroxyphenyl)ethyl, β-(3-benzyl-5-methyl-4-hydroxyphenyl)ethyl, β-(3-t-butyl-4-hydroxyphenyl)ethyl, β-(2-methyl-3,5-di-t-butyl-4-hydroxyphenyl)ethyl, β-(3,5-diisopropyl-4-hydroxyphenyl)ethyl, γ-(3,5-di-t-butyl-4-hydroxyphenyl)propyl, γ-(3-methyl-5-t-butyl-4-hydroxyphenyl)propyl, α-methyl-γ-(3,5-di-t-butyl-4-hydroxyphenyl)propyl, or ε-(3-t-butyl-4-hydroxyphenyl)pentyl.

Among the more preferred tertiary amides of the invention are (1) the N,N-bis[β-(3,5-di-t-butyl-4-hydroxyphenyl)ethyl ]acetamide, N,N-bis[β-(3,5-di-t-butyl-4-hydroxyphenyl)ethyl]stearamide, N,N-bis[β-(3,5-diisopropyl-4-hydroxyphenyl)ethyl]acetamide, and N,N-bis[β-(3-methyl-5-t-butyl-4-hydroxyphenyl)ethyl-]acetamide monoamides, (2) the N,N,N',N'-tetrakis[β-(3,5-di-t-butyl-4-hydroxyphenyl)ethyl]- and N,N,N',N'-tetrakis[β-(3-methyl-5-t-butyl-4-hydroxyphenyl)ethyl]-glutaramide, terephthalamide, succinamide, and adipamide bisamides, (3) the N,N,N',N',N'',N''-hexakis[β-(3,5-di-t-butyl-4-hydroxyphenyl)ethyl]-and N,N,N',N',N'',N''-hexakis[β-(3methyl-5-t-butyl-4-hydroxyphenyl)ethyl]-1, 3,5-benzenetricarboxamides, and (4) the N,N-bis[β-(3,5-di-t-butyl-4-hydroxyphenyl-)ethyl]-, N,N-bis[β-(3,5-diisopropyl-4-hydroxyphenyl-)ethyl]-, and N,N-bis[β(3-methyl-5-t-butyl-4-hydroxyphenyl)ethyl]methanesulfonamides.

The most preferred of the tertiary amides are apt to be N,N-bis[β-(3,5-di-t-butyl-4-hydroxyphenyl)ethyl-]acetamide, N,N-bis[β-(3,5-di-t-butyl-4-hydroxyphenyl-)ethyl]methanesulfonamide, N,N,N',N'-tetrakis[β-(3,5-di-t-butyl-4-hydroxyphenyl)ethyl]glutaramide, N,N,N',N'-tetrakis[β-(3,5-di-t-butyl-4-hydroxyphenyl-)ethyl]terephthalamide, and N,N,N',N',N'',N''-hexakis[β-(3,5-di-t-butyl-4-hydroxyphenyl)ethyl]-1,3,5-benzenetricarboxamide—the particular tertiary amide preferred in any specific instance depending on the needs of the particular organic material being stabilized.

The tertiary amides may be prepared by reacting the appropriate acyl or sulfonyl halide corresponding to the formula $R(QX)_n$ with the appropriate secondary amine corresponding to the formula:

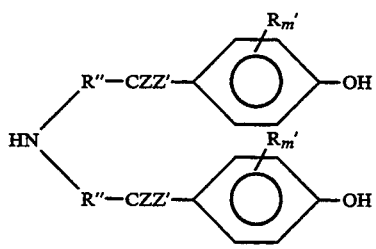

X representing halo, preferably chloro or bromo; and R, R', R'', Q, Z, Z', m, and n being as previously defined. Thus, for example, (1) an acyl halide such as acetyl chloride, propionyl chloride, butyryl bromide, isobutyryl chloride, stearoyl chloride, or benzoyl chloride, (2) a dicarboxylic acid dihalide such as glutaryl dichloride, malonyl dichloride, adipyl dibromide, succinyl dichloride, terephthaloyl dichloride, isophthaloyl dichloride, cyclopentane-1,3-dicarboxylic acid dibromide, cyclohexane-1,4-dicarboxylic acid dichloride, 1,12-dodecanedicarboxylic acid dichloride, or 1,14-tetradecanedicarboxylic acid dichloride, (3) a tricarbonyl trihalide such as a 1,2,4- or 1,3,5-benzenetricarbonyl trichloride, 1,2,3-propanetricarbonyl tribromide, or 2,3-dimethyl-1,2,3-butanetricarbonyl trichloride, or (4) a sulfonyl halide such as methanesulfonyl chloride, 1-butanesulfonyl bromide, 1-pentanesulfonyl chloride, 1-decanesulfonyl chloride, or benzenesulfonyl chloride is reacted with a secondary amine such as bis[β-(3,5-di-t-butyl-4-hydroxyphenyl)ethyl]amine, bis[γ-(3-methyl-5-t-butyl4-hydroxyphenyl)propyl]amine, or other such amine.

In the synthesis of the tertiary amides, the amines and acid halides are reacted in substantially stoichiometric amounts in a solvent which is inert to the reaction and which is capable of solubilizing both the reactants and the product and optionally in the presence of an acid scavenger which can neutralize acid produced by the reaction without adversely affecting the process.

Solvents suitable for use in the reaction include, e.g., toluene, benzene, xylene, mesitylene, pentane, hexane, heptane, octane, chlorobenzene, methylene chloride, chloroform, carbon tetrachloride, 1,2-dichloroethane, 1,1,2-trichloroethane, diethyl ether, and petroleum ether, the preferred solvents usually being toluene and methylene chloride.

Examples of acid scavengers which may be used in the process are trimethylamine, triethylamine, tripropylamine, tributylamine, pyridine, 4-dimethylaminopyridine, and 2,6-lutidine, with the preferred acid scavenger being triethylamine. When employed, the acid scavenger is used in an amount such as to provide about one mol of acid scavenger per mol of acid generated by the reaction.

In the preparation of the tertiary amides, the components of the reaction mixture are combined in any suitable way, conveniently by slowly adding a solution of the amine (and optionally also an acid scavenger) in a portion of the solvent to a solution of the acid halide in the remainder of the solvent while maintaining the reaction mixture at a temperature of 0°–25° C. Then, when combination of the reactants is at least substantially complete, the temperature is raised, if necessary, to be in the range of 10°–45° C., preferably 25°–35° C., and kept in that range for a suitable time, e.g., 2–10 hours. It is ordinarily most convenient in this reaction to use ambient temperature.

After completion of the reaction, the product can be recovered in any appropriate way. For example, the reaction mixture may be diluted with solvent, preferably the same solvent as was used in the reaction; the diluted reaction mixture may then be washed with an inorganic acid, such as HCl; the organic phase resulting from this wash may be recovered and washed with a base, such as NaOH; the organic phase resulting from this wash may be recovered and washed with a salt solution, e.g., aqueous NaCl; and the organic phase resulting from this wash may be recovered and dried to yield the desired tertiary amide.

In an embodiment of the invention, the tertiary amides are used as antioxidants for organic materials which are normally susceptible to oxidative deterioration, such as the organic materials taught in Knell, Huber-Emden et al., Gencarelli et al., and Schmidt et al.

Although the organic materials that can be stabilized in the practice of the invention include various materials such as fuels, hydrocarbon and ester lubricants, plasticizers, epoxy resins, polycarbonates, polyurethanes, polyureas, polyamides, polyesters, polyethers, phenol-formaldehyde resins, urea-formaldehyde resins, melamineformaldehyde resins, and natural polymers (e.g., cellulose, rubber, proteins, and their derivatives), those which are apt to be most beneficially stabilized are synthetic polymers such as:

(1) polymers and interpolymers of ethylenically-unsaturated hydrocarbons, such as ethylene, propylene, butylene, isobutylene, styrene, butadiene, and piperylene, including the homopolymers, copolymers, and other interpolymers thereof with one another, and copolymers and interpolymers of at least one of them with one or more copolymerizable non-hydrocarbons, such as vinyl acetate, acrylonitrile, methacrylonitrile, methyl acrylate, and methyl methacrylate, (2) halogen-containing polymers, such as polyvinyl chloride and fluoride, polyvinylidene chloride, vinyl chloride-vinylidene chloride copolymers, polychloroprene, and chlorinated rubbers, (3) other vinyl and allyl polymers, such as polyvinyl alcohol, acetate, stearate, benzoate, maleate, and butyral, polyallylmelamine, and polyallyl phthalate, and (4) acrylic polymers, such as polyacrylates, polymethacrylates, polyacrylamides, polyacrylonitrile, and polymethacrylonitrile.

In a particularly preferred embodiment of the invention, the tertiary amides are used to stabilize thermoplastic polymers, such as polyethylenes, polypropylenes, and polycarbonates, during processing, e.g., extrusion or injection molding.

The tertiary amides are combined with the normally oxidable materials in antioxidant amounts, usually an amount in the range of 0.005-5%, preferably 0.01-2%, based on the weight of the organic material.

When used as antioxidants, the tertiary amides may be employed as the sole stabilizers for the normally-oxidizable organic materials, or they may be used in conjunction with other stabilizers, such as conventional phenolic antioxidants or thioester synergists. Moreover, their activity as antioxidants does not appear to be inhibited by the presence in the organic materials of additives such as those conventionally employed in such materials, e.g., light stabilizers, ultraviolet light absorbers, metal deactivators, pigments, dyes, lubricants, nucleating agents, and fillers.

In general, all of the tertiary amides of the invention are good processing stabilizers. However, those having the higher molecular weights—typically also having lower volatility and greater thermal stability—are superior when high processing temperatures and/or long-term stabilization are required, while those having the lower molecular weights—typically also having lower melting points—are more suitable for use when low-to-moderate processing temperatures are required.

The following examples are given to illustrate the invention and are not intended as a limitation thereof. Unless otherwise specified, quantities mentioned in the examples are quantities by weight. Code names are sometimes used in these examples to identify compounds as shown in Table I.

TABLE I

| Compound | Code Name |
| --- | --- |
| 1,3,5-tris(3,5-di-t-butyl-4-hydroxybenzyl)-2,4,6-trimethylbenzene - a commercially-available antioxidant sold by Ethyl Corporation as Ethanox ® 330 | E-330 |
| N,N-bis(3,5-di-t-butyl-4-hydroxybenzyl)acetamide - a compound taught by Nikiforov et al. | N-1190 |
| N,N-bis[β-(3,5-di-t-butyl-4-hydroxyphenyl)ethyl]-2,2,2-trichloroacetamide - a compound taught by Cornell | C-1176 |
| Bis[β-(3,5-di-t-butyl-4-hydroxyphenyl)ethyl]amine - a reactant used in preparing products of the Examples | S-1161 |
| N,N-bis[β-(3,5-di-t-butyl-4-hydroxyphenyl)ethyl]acetamide | AN-1162 |
| N,N,N',N'-tetrakis[β-(3,5-di-t-butyl-4-hydroxyphenyl)ethyl]glutaramide | AN-1163 |
| N,N,N',N'-tetrakis[β-(3,5-di-t-butyl-4-hydroxyphenyl)ethyl]terephthalamide | AN-1164 |
| N,N-bis[β-(3,5-di-t-butyl-4-hydroxyphenyl)ethyl]methanesulfonamide | AN-1168 |
| N,N,N',N',N'',N''-hexakis[β-(3,5-di-t-butyl-4-hydroxyphenyl)ethyl]-1,3,5-benzenetricarboxamide | AN-1178 |

EXAMPLE 1

Preparation of AN-1162

Charge a suitable reaction vessel with 1.6 g of acetyl chloride and 10 mL of dry toluene. While stirring the reaction mixture and maintaining the temperature at 0°-8° C., slowly add a solution of 9 g of S-1161, 2.1 g of triethylamine, and 30 mL of dry toluene. Then allow the reaction mixture to reach ambient temperature and maintain that temperature for four hours.

After completion of the four-hour period, wash the reaction mixture consecutively with 50 mL of 3N HCl, 50 mL of 1N NaOH, and 50 mL of a saturated aqueous NaCl solution, the organic phase being recovered after each wash and then subjected to the next wash. Recover the final washed organic phase, dry, and concentrate in vacuo to provide a 98% yield of N,N-bis[β-(3,5-di-t-butyl-4-hydroxyphenyl)ethyl]acetamide.

Recrystallize the crude product from 100 mL of heptane and wash the precipitated product with 75 mL of heptane. GC analysis shows the recrystallized product to contain 99% of the tertiary amide, which has a melting point of 153°-155° C. Spectral analyses (H-NMR, $^{13}$C-NMR, IR, GC-MS) confirm the identity of the solid as N,N-bis[β-(3,5-di-t-butyl-4-hydroxyphenyl)ethyl]acetamide.

EXAMPLE 2

Preparation of AN-1168

Repeat Example 1 except for replacing the acetyl chloride with 2.9 g of methanesulfonyl chloride and using 2.7 g of the triethylamine. Prior to the recrystallization of the crude product from heptane, it contains 97.6 area % of N,N-bis[β-(3,5-di-t-butyl-4-hydroxyphenyl)ethyl]methanesulfonamide. After recrystallization, GC analysis shows the product to contain >99% of the tertiary sulfonamide, which has a melting point of 132°-134° C. Spectral analyses (H-NMR, $^{13}$C-NMR, IR, GC-MS) confirm the identity of the solid as N,N-bis[β-(3,5-di-t-butyl-4-hydroxyphenyl)ethyl]methanesulfonamide.

EXAMPLE 3

Preparation of AN-1163

Charge a suitable reaction vessel with 1.78 g of glutaryl dichloride and 10 mL of dry toluene. While stirring the reaction mixture and maintaining the temperature at 0°-8° C., slowly add a solution of 10.1 g of S-1161, 2.31 g of triethylamine, and 30 mL of dry toluene. Then allow the reaction mixture to reach ambient temperature and maintain that temperature for four hours.

After completion of the four-hour period, dilute the reaction mixture with 50 mL of toluene and wash it consecutively with 50 mL of 3N HCl, 50 mL of 1N NaOH, and 50 mL of a saturated aqueous NaCl solution, the organic phase being recovered after each wash and then subjected to the next wash. Recover the final washed organic phase, dry it, and concentrate it on a rotary evaporator to provide 11.4 g of product.

Dissolve the product in 350 mL of heptane at 100° C. and recrystallize it at 0° C. to provide 9.9 g of recrystallized product. TLC analysis shows the recrystallized product to contain 98.1 area % of N,N,N',N'-tetrakis[β-(3,5-di-t-butyl-4-hydroxyphenyl)ethyl]glutaramide, which has a melting point of 167°-169° C. The yield is 92%, and spectral analyses (H-NMR, IR, HRMS, and $^{13}$C-NMR) confirm the structure of the product.

EXAMPLE 4

Preparation of AN-1164

Repeat the reaction of Example 3 except for replacing the glutaryl dichloride with 2.09 g of terephthaloyl dichloride to provide 11.4 g of product. Stir the product in 100 mL of refluxing heptane for one hour, cool to room temperature, and isolate the precipitated product by filtration. Recrystallize the product from a mixture of 200 mL of heptane and 160 mL of toluene to provide 9.2 g of recrystallized product. TLC analysis shows this product to contain 99.0 area % of N,N,N',N'-tetrakis[β-(3,5-di-t-butyl-4-hydroxyphenyl)ethyl ]terephthalamide, which has a melting point of 208°-210° C. The yield is 83%, and spectral analyses (H-NMR, IR, HRMS, and $^{13}$C-NMR) confirm the structure of the product.

EXAMPLE 5

Preparation of AN-1178

Slowly add a solution of 10.1 g of S-1161 and 2.3 g of triethylamine in 50 mL of dry toluene to a stirred solution of 1.8 g of 1,3,5-benzenetricarbonyl trichloride in 15 mL of dry toluene maintained at 0°-8° C. Then warm the reaction mixture to room temperature and stir overnight to provide 11.7 g of product.

After completing the overnight stir, dilute the reaction mixture with 50 mL of toluene and wash it consecutively with 50 mL of 3N HCl, 50 mL of 1N NaOH, and 50 mL of a saturated aqueous NaCl solution, the organic phase being recovered after each wash and then subjected to the next wash. Recover the final washed organic phase, dry it, and concentrate it on a rotary evaporator to provide 11.7 g of product.

Stir the crude product in refluxing heptane for 15 minutes, cool, and isolate the precipitated solids by filtration. Recrystallize the resulting 10.3 g of solids in 100 mL of ethanol and then from a mixture of 100 mL of heptane and 70 mL of toluene. TLC analysis shows this product to contain 97.5 area % of N,N,N',N',N'',N''-hexakis[β-(3,5-di-t-butyl-4-hydroxyphenyl)ethyl]-1,3,5-benzenetricarboxamide, which has a melting point of 193°-195° C. The yield is 58%, and spectral analyses (H-NMR, IR, HRMS, and $^{13}$C-NMR) confirm the structure of the product.

EXAMPLE 6

Determination of Volatility and Thermal Stability

Subject the products of Examples 1-5 to thermogravimetric analysis by heating different samples of the products at 10° C./minute from 25° C. under nitrogen and air, respectively, to determine the temperatures at which there is a 10% weight loss. The results of the analyses are shown in Table II.

TABLE II

| Example | Compound | °C. in Nitrogen at 10% Weight Loss | °C. in Air at 10% Weight Loss |
|---------|----------|-----------------------------------|------------------------------|
| 1 | AN-1162 | 298 | 282 |
| 2 | AN-1168 | 293 | 293 |
| 3 | AN-1163 | 359 | 343 |
| 4 | AN-1164 | 359 | 342 |
| 5 | AN-1178 | 357 | 348 |

When N-1190, a compound which has a chain of less than two carbons between the alkyl-substituted hydroxyphenyl groups and the amido nitrogen, is subjected to the same analysis, the analytical results show the temperatures at which a 10% weight loss is found in nitrogen and air are 245° C. and 249° C., respectively. This demonstrates the lower volatility and the superior thermal stability of the amides of the invention.

EXAMPLE 7

Evaluation of Antioxidants in Polypropylene

Part A

Prepare two series of polypropylene compositions by (1) blending two different samples of Profax ® 6501, a product of Himont Incorporated, with 0.05% of calcium stearate as an acid neutralizer and lubricant, (2) dividing each of these blends into aliquots, and (3) blending each of the aliquots to be stabilized with 0.1% of an antioxidant. The antioxidants used in the blends are:

| Blend | Antioxidant |
|-------|-------------|
| A-1 | C-1176 |
| A-2 | N-1190 |
| A-3 | E-330 |
| A-4 | AN-1162 |
| A-5 | AN-1178 |
| B-1 | none |
| B-2 | E-330 |
| B-3 | AN-1162 |
| B-4 | AN-1163 |
| B-5 | AN-1164 |
| B-6 | AN-1168 |

Part B

Test the compositions of Part A for melt flow index and yellowness index by extruding them in a Brabender twin screw extruder at 150°–245°—245° C. and 30 rpm under nitrogen and then making five passes through a Brabender single screw extruder at 260°—260°—260°—260° C. and 30 rpm with ambient air. The test results are shown in Table III.

TABLE III

| Blend | MFI @ 230° C./ 2160 g Load Extrusion Passes | | | | Yellowness Index Extrusion Passes | | |
|---|---|---|---|---|---|---|---|
| | TwS | ss1 | ss3 | ss5 | ss1 | ss3 | ss5 |
| A-1 | 4.7 | 5.0 | 6.3 | 7.4 | 6.2 | 10.0 | 15.0 |
| A-2 | 4.7 | 5.2 | 6.5 | 9.0 | 5.3 | 6.7 | 9.3 |
| A-3 | 3.7 | 6.0 | 10.4 | 15.5 | 4.2 | 5.8 | 6.8 |
| A-4 | 5.2 | 6.5 | 9.0 | 13.2 | 5.0 | 6.4 | 7.9 |
| A-5 | 4.8 | 6.4 | 11.8 | 16.3 | 4.0 | 5.7 | 6.9 |
| B-1 | 9.6 | 28.5 | 96.5 | — | 3.1 | 5.8 | — |
| B-2 | 4.3 | 5.9 | 8.3 | 10.8 | 4.9 | 7.3 | 10.9 |
| B-3 | 4.3 | 4.9 | 6.9 | 8.3 | 5.5 | 9.0 | 12.0 |
| B-4 | 4.8 | 5.8 | 6.7 | 8.3 | 5.9 | 10.7 | 15.2 |
| B-5 | 4.7 | 5.7 | 7.4 | 9.6 | 6.0 | 9.1 | 12.8 |
| B-6 | 4.3 | 6.1 | 8.4 | 10.9 | 5.5 | 9.1 | 12.4 |

Part C

Test the compositions of Part A for resistance to failure on oven aging by (1) molding pellets of the compositions retained from the twin screw pass of Part B into plaques having a thickness of ~0.06 cm, using a hydraulic press set at 245° C. for the molding, (2) cutting each of the plaques into five ~2.5 cm squares, (3) placing each of the squares into glass Petri dishes, (4) placing the Petri dishes into an air-circulating oven set at 150° C., and (5) checking the samples every 24 hours for failure—failure being determined when at least three of the five squares of a particular composition are visually decomposed. The test results are shown below.

| Blend | Total Hours @ Failure |
|---|---|
| A-1 | 120 |
| A-2 | 48 |
| A-3 | 384 |
| A-4 | 96 |
| A-5 | 576 |
| B-1 | 24 |
| B-2 | 336 |
| B-3 | 96 |
| B-4 | 864 |
| B-5 | 840 |
| B-6 | 120 |

As demonstrated in the preceding examples, the tertiary amides of the invention include a variety of compounds which (1) have utility in stabilizing organic materials against deterioration during processing and oven aging, (2) have melting points sufficiently lower than the 240°–245° C. melting point of E-330 to make them preferable to that commercial antioxidant for use in low-to-moderate temperature processing, (3) have greater thermal stability than amides such as N-1190, and (4) in general, compare favorably with known antioxidants as stabilizers for organic materials which are normally susceptible to oxidative deterioration. Those which have the least tendency toward developing color bodies are particularly valuable for stabilizing organic materials, such as some of the organic polymers, that are to be used in applications wherein the impartation of color would be undesirable. Those which show greater tendencies to form color are more apt to be useful in stabilizing organic materials in which color is not a disadvantage, e.g., fuels, lubricants, and some organic polymers.

I claim:

1. A tertiary amide corresponding to the formula:

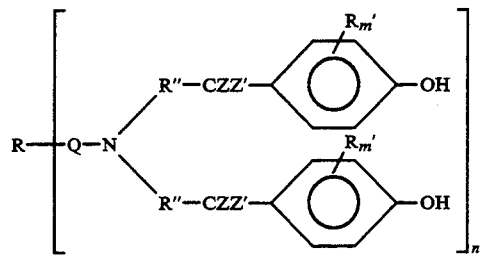

wherein R is a di or trivalent aromatic or saturated aliphatic hydrocarbon group containing 1–20 carbons; n is an integer of 2–3 which is equal to the valence of R; R' is phenyl, benzyl, or $C_1$–$C_6$ alkyl; m is an integer of 1–3; R'' is a $C_1$–$C_4$ alkylene group; Z and Z' are independently selected from hydrogen and alkyl; and Q is carbonyl.

2. The tertiary amide of claim 1 wherein n is 2.

3. The tertiary amide of claim 2 which is an N,N,N',N'-tetrasubstituted glutaramide wherein R' is an alkyl group of 1–4 carbons, m is 2, and CZZ'R'' is $(CH_2)_p$ in which p is an integer of 2–5.

4. The tertiary amide of claim 3 which is N,N,N',N'-tetrakis[β-(3,5-di-t-butyl-4-hydroxyphenyl) ethyl]-glutaramide.

5. The tertiary amide of claim 2 which is an N,N,N',N'-tetrasubstituted terephthalamide wherein R' is an alkyl group of 1–6 carbons, m is 2, and CZZ'R'' is $(CH_2)_p$ in which p is an integer of 2–5.

6. The tertiary amide of claim 5 which is N,N,N',N'-tetrakis[β-(3,5-di-t-butyl-4-hydroxyphenyl)ethyl]-terephthalamide.

7. The tertiary amide of claim 1 wherein n is 3.

8. The tertiary amide of claim 7 which is an N,N,N',N',N'',N''-hexasubstituted 1,3,5-benzenetricarboxamide wherein R' is an alkyl group of 1–4 carbons, m is 2, and CZZ'R'' is $(CH_2)_p$ in which p is an integer of 2–5.

9. The tertiary amide of claim 8 which is N,N,N',N',N'',N'''-hexakis[β-(3,5-di-t-butyl-4-hydroxyphenyl)ethyl ]-1,3,5 -benzenetricarboxamide.

10. A composition comprising an organic material selected from the group consisting of a fuel, hydrocarbon lubricant, ester lubricant, plasticizer, synthetic polymer and natural polymer and an antioxidant amount of a tertiary amide corresponding to the formula:

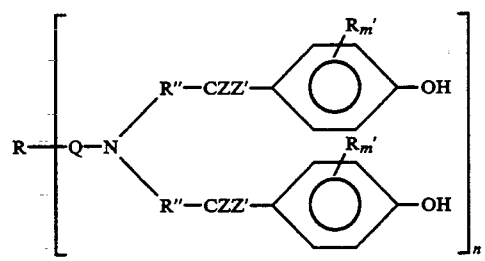

wherein R is a di- or trivalent aromatic or saturated aliphatic hydrocarbon group containing 1–20 carbons, n is an integer of 2 or 3 which is equal to the valence of R; R' is phenyl, benzyl, or $C_1$–$C_6$ alkyl; m is an integer of 1–3; R" is a $C_1$–$C_4$ alkylene group; Z and Z' are independently selected from hydrogen and alkyl; and Q is carbonyl.

11. The composition of claim 10 wherein the organic material which is normally susceptible to oxidative deterioration is a polymer of an ethylenically-unsaturated hydrocarbon.

12. The composition of claim 11 wherein the tertiary amide is an N,N,N',N',N",N"-hexasubstituted 1,3,5-benzenetricarboxamide in which R' is an alkyl group of 1–6 carbons, m is 2, and CZZ'R" is $(CH_2)_p$ in which p is an integer of 2–5.

13. The composition of claim 12 wherein the tertiary amide is N,N,N',N',N",N"-hexakis[β-(3,5-di-t-butyl-4-hydroxyphenyl)ethyl]-1,3,5-benzenetricarboxamide.

* * * * *